United States Patent [19]

Slaugh

[11] 4,229,320
[45] Oct. 21, 1980

[54] CATALYST FOR MAKING PARA-XYLENE

[75] Inventor: Lynn H. Slaugh, Houston, Tex.

[73] Assignee: Shell Oil Company, Houston, Tex.

[21] Appl. No.: 5,653

[22] Filed: Jan. 22, 1979

[51] Int. Cl.$^3$ .................. B01J 21/04; B01J 21/08; B01J 23/04; B01J 23/14; B01J 23/36
[52] U.S. Cl. .................................. 252/454; 252/463; 252/476; 585/417
[58] Field of Search .................. 252/454, 463, 476; 585/417

[56] References Cited

U.S. PATENT DOCUMENTS

| | | | |
|---|---|---|---|
| 3,291,564 | 12/1966 | Kearby | 252/463 X |
| 3,755,556 | 8/1973 | Aldridge | 252/476 X |
| 3,830,866 | 8/1974 | D'Alessandro et al. | 585/417 |

Primary Examiner—W. J. Shine

[57] ABSTRACT

Isobutylene is selectively converted to para-xylene over a coupling catalyst consisting essentially of a neutral or weakly acidic support impregnated with a non-halogen containing water soluble rhenium compound and an alkali metal hydroxide or stannate and then reduced with hydrogen at elevated temperatures.

6 Claims, No Drawings

CATALYST FOR MAKING PARA-XYLENE

BACKGROUND OF THE INVENTION

This invention relates to a process for the preparation of p-xylene as well as the catalytic composition used therein. More particularly, this invention is directed toward a process for the selective conversion of isobutylene to p-xylene over a supported catalyst impregnated with a non-halogen containing water soluble rhenium compound and an alkali metal hydroxide or stannate and then reduced with hydrogen at elevated temperatures.

Dehydrocoupling reactions, such as the conversion of isobutylene to various aromatics, are of interest as a means of utilizing the isobutylene often produced in large amounts as a by-product of such commercial refining processes as hydrocarbon cracking. It would be especially desirable to selectively convert an isobutylene feed to para-xylene while avoiding the formation of ortho-xylene and meta-xylene isomers. Para-xylene is the more valuable xylene isomer and finds applications as an octane booster in motor fuels or as a precursor to commercially important intermediates such as terephthalic acid. While other aromatics like benzene or toluene that may be formed are comparatively easy to distill off, the separation of the xylene isomers is more difficult, requiring costly recrystallization and filtration which may often prove impractical in large scale operations. With the instant invention, a simple and effective process has been devised to obtain the desired para-xylene product in the absence of the troublesome meta- and/or ortho-isomers.

The prior art discloses several methods for the preparation of aromatics from aliphatic or olefinic hydrocarbon streams with the use of catalysts containing some form of rhenium. For example, U.S. Pat. No. 3,546,138 discloses a catalyst consisting of oxides of antimony and iron promoted with an oxide of rhenium for use in the oxidative dehydrogenation of olefins to diolefins and aromatics. However, it is specifically mentioned that isobutylene should not be in the feed in large amounts. U.S. Pat. No. 3,856,880 discloses the use of rhenium to promote ferrite catalysts for the oxidative dehydrogenation of organic compounds; the conversion of a pentene to a mixture of xylenes is specifically taught. In U.S. Pat. No. 3,374,281, a catalyst consisting of an acidic support with a metal or oxide of a metal such as rhenium as a dehydrogenation component is disclosed for the conversion of paraffinic hydrocarbons to various alkylated aromatics. Similarly, a form of rhenium is employed in the catalyst in the following U.S. Pat. Nos. patents which disclose cyclization or aromatization reactions: 4,003,957; 3,855,115; 3,541,001 and 3,129,243. It should be noted that the listed patents do not describe the selective conversion of an olefinic stream to a single xylene isomer. The prior art which utilizes a rhenium component often does so in conjunction with some other metal and nowhere discloses further treatment with an alkali metal hydroxide or stannate as herein.

The selective production of p-xylene from isobutylene and/or other olefinic charge stocks is disclosed in the following patents: U.S. Pat. Nos. 4,007,231; 3,830,866; 3,769,237; 3,730,957; 3,644,551 and 3,644,550. However, none of these patents disclose catalysts containing any form of a rhenium component. Serious corrosion problems may also arise in some cases from compounds that are added to the catalyst to promote the dehydrocoupling reaction which yields the p-xylene isomer.

The prior art also discloses catalysts which contain rhenium for the isomerization of xylene isomers to p-xylene. See for example U.S. Pat. Nos. 3,642,925 and 3,557,022 and German Pat. No. 2,221,863. These three patents again teach the presence of additional metals, such as platinum or tin, in the catalytic compositions. Furthermore, an isomerization reaction differs radically from the types of coupling reactions claimed herein.

SUMMARY OF THE INVENTION

A process has now been discovered for the selective conversion of isobutylene to p-xylene over a novel coupling catalyst comprising rhenium in oxide or metallic form deposited on a neutral or weakly acidic support which has been additionally impregnated with an alkali metal hydroxide or stannate and subsequently reduced with hydrogen at elevated temperatures. The rhenium is provided by a non-halogen containing water soluble rhenium compound which is reduced after deposit on said support. This process provides a means for obtaining the more valuable p-xylene isomer from the olefinic feed stream while avoiding the troublesome formation of the ortho-xylene and meta-xylene isomers. The catalytic composition obviates the problems of low selectivity, commercial infeasibility or system corrosion obtained with catalysts in the prior art. By producing solely the para-xylene isomer, the costly and impractical recrystallization normally required for the separation of the three xylene isomers is avoided. The catalyst is conveniently prepared in a two step process where the non-halogen containing water-soluble rhenium compound and an alkali metal hydroxide or stannate are deposited on the appropriate support and the rhenium component is subsequently reduced by treatment with hydrogen at elevated temperatures. It is believed that the catalysts prepared in this manner contain sites which promote the dimerization of isobutylene selectively to a 2,5-dimethylhexyl structure which leads exclusively to the para-isomer of xylene.

DESCRIPTION OF THE PREFERRED EMBODIMENTS

Suitable supports for the coupling catalysts above are such neutral or weakly acidic supports as silicas and alumina, many of which are commercially available. Alumina is the support of choice. Generally, highly acidic supports should be avoided as they may cause some undesired isomerization. Silica-alumina supports and zeolites are examples of supports which may cause isomerization problems. The support is suitably impregnated with a non-halogen containing water soluble rhenium compound. Ammonium perrhenate and rhenium heptaoxide are the rhenium compounds of choice. Halogenated rhenium compounds are too acidic in nature, causing undesirable side reactions. As will be more fully discussed below, the rhenium compound is deposited on the support by reaction with a warm aqueous solution of the rhenium compound and subsequently calcined with air. The supported rhenium catalyst is also treated (doped) with an alkali metal hydroxide or stannate. Sodium or potassium are the preferred alkali metals; thus sodium hydroxide, sodium stannate, potassium hydroxide or potassium stannate are the preferred compounds for doping the catalyst in this manner. Of these, sodium hydroxide and sodium stannate are more preferred. After both components are deposited on the support, the composition is then treated with hydrogen at elevated temperatures. This treatment serves to reduce the rhenium component to its metallic state while leaving the hydroxide or stannate largely unreduced. Accordingly, the preferred catalytic composition herein is an alumina support impregnated with rhenium heptaoxide or ammonium perrhenate, calcined, additionally treated with sodium hydroxide or sodium stannate and finally reduced with hydrogen at elevated temperatures. The process according to the invention may be carried out batchwise or continuously and is suitably conducted by passing the isobutylene reactant, optionally and preferably in the presence of an inert diluent gas such as nitrogen, into a reaction zone containing the supported rhenium catalyst as a fixed or fluidized bed at elevated temperatures and recovering the p-xylene formed from the reaction zone effluent.

The support is impregnated with the non-halogen containing rhenium compound by completely wetting the surface of the support with a warm aqueous solution of the desired rhenium compound. The wet particles are transferred to a reaction tube and calcined with a flowing stream of an oxygen-containing gas e.g., air. Temperatures, are typically increased each quarter-hour in 50° increments, to a final temperature of 500° C. If desired, the catalyst may be reduced by heating in a similar manner with a flowing nitrogen stream, followed by a hydrogen stream when the temperature reaches 200° C. Final temperature for the reduction will typically be 550° C. The amount of the rhenium compound deposited on the support is typically about 0.2 to about 20% by weight, in terms of rhenium metal itself, with a preferred range of about 2 to about 5% by weight.

The unreduced supported rhenium catalyst is additionally treated with an aqueous solution of an alkali metal hydroxide or stannate, preferably an aqueous solution of sodium hydroxide, sodium stannate, potassium hydroxide or potassium stannate. If an alkali metal hydroxide is used, it is typically present on the catalyst in amounts from about 2.4 to about 14% by weight, and preferably from about 4 to about 8% by weight. If an alkali metal stannate is used, it is typically present on the catalyst in amounts of from about 5 to about 15% by weight, with preferred amounts from about 5 to about 10% by weight. If the rhenium compound used to impregnate the catalyst also contained an alkali metal, for example sodium perrhenate, it is desirable to take its presence into account when calculating the appropriate amount of alkali metal hydroxide or stannate to add in the additional treatment. Although the rhenium component is normally the first to be deposited on the support, the catalyst may also be prepared by depositing the alkali metal hydroxide or stannate on the support prior to treatment with the non-halogen containing water-soluble rhenium compound. After the support is impregnated with both components in the described manner, the catalyst is again dried and reduced with hydrogen at elevated temperatures in a reactor tube, optionally and preferably in the presence of an inert diluent gas such as nitrogen or argon, most preferably nitrogen. As before, the hydrogen stream is typically introduced when the temperature reaches 200° C. and the temperature typically is raised in the same increments and durations. The maximum reduction temperature is preferably 550° C.

In the process according to the invention, the catalyst as prepared above is loaded in a reactor tube and the isobutylene reactant passed through the tube, optionally and preferably with a concurrent stream of an inert diluent gas as above. The product stream containing p-xylene is then collected by conventional means, for example, condensation in externally cooled heat exchangers. The reaction may be suitably conducted at pressures ranging from atmospheric pressure to 1000 psig, most preferably from atmospheric pressure to 200 psig. The reaction suitably takes place at elevated temperatures of from 400° to 600° C., with temperatures of 450° to 550° C. preferred. Above temperatures of 550° C., small amounts of other xylene isomers may begin to contaminate the desired p-xylene. Methane and isobutane are the main by-products of the reaction. The isobutane may be dehydrogenated to yield isobutylene and fed through the reactor tube again so as to increase the total level of conversion to p-xylene. Alternatively, the by-products each may be utilized as a feed for a number of conventional processes whereby they are converted to more valuable chemicals or intermediates. Minor amounts of benzene, toluene and other $C_2$–$C_4$ saturated and unsaturated hydrocarbons also are produced. The amounts and types of by-products which result are highly dependent on reaction conditions and temperature. The desired p-xylene may also be separated from the various by-products by conventional means such as distillation. The previous concern that distillation would not separate mixtures of xylene isomers has been obviated by the catalyst of the instant invention which, in its preferred embodiments, allows selective production of only the para-xylene isomer.

If desired, the catalyst may be regenerated by slow oxidation with a flowing air stream while temperatures are gradually increased to 550° C. The catalyst is then reduced with hydrogen at elevated temperatures as before, optionally and again preferably in the presence of a concurrent stream of an inert diluent gas. Thus, there is provided herein a catalytic composition and its use in a process for the selective conversion of an abundant olefin such as isobutylene to the more valuable p-xylene, while avoiding the troublesome formation of other xylene isomers. The invention is illustrated further in the following examples, which are not to be construed as limiting its scope. In all examples, the specified size of the vycar reactor tube refers to the inside diameter of the tube.

EXAMPLE I

Approximately 48 grams of an 18–30 mesh alumina support (Reynolds RA-1 alumina, surface area of 264 square meters per gram) was impregnated with 20 milliliters of a warm aqueous solution containing 2.8 grams of ammonium perrhenate, which was sufficient to completely wet the surface. The wet particles were placed in an 18 millimeter vycar tube and heating begun in the presence of a downward air stream of 400 milliliters/minute. Temperatures were increased in 50° C. increments approximately every 15 minutes until a final temperature of 500° C. was attained.

EXAMPLE II

The catalyst from Example I, now in a similar 11 millimeter vycar reactor tube, was reduced in the following manner. The catalyst was heated to 200° C. in the presence of a downward nitrogen flow of 200 milliliters/minute. A hydrogen flow of 100 milliliters/minute was then added and the temperature raised in increments as in Example I, up to a final temperature of 550° C.

EXAMPLE III

Approximately 10 grams of the unreduced catalyst from Example I was treated with 4 milliliters of an aqueous solution containing 0.87 grams of sodium stannate. The particles were subsequently loaded in an 11 millimeter vycar tube for drying and reduction. Under a nitrogen flow of 200 milliliters/minute, the temperature was increased in 50° increments approximately every 15 minutes. When the temperature reached 200° C., a hydrogen flow of 100 milliliters/minute was added and heating continued in the same manner to a final temperature of 550° C.

EXAMPLE IV

Approximately 10 grams of the unreduced catalyst from Example I was treated with 4 milliliters of an aqueous solution containing 0.5 grams of sodium hydroxide. Drying and reduction then proceeded as in Example III.

EXAMPLES V–VII

Approximately 10 cubic centimeters of catalyst was loaded into an 11 millimeter vycar tube, with 5 milliliters of quartz chips placed above each catalyst bed. Catalysts prepared in the general manners described in Examples II, III and IV were used for Examples V, VI and VII, respectively. The upper end of each reaction tube was fitted with a combination inlet for nitrogen, hydrogen and isobutylene. Approximately 40 milliliters/minute of nitrogen, and 40 milliliters/minute of isobutylene were fed through each reactor tube at temperatures of either 550° or 600° C. The product stream exiting from each reactor tube passed into mass spectroscopy tubes, a wet test meter and a dry ice-acetone chilled trap. The distribution of products was determined via gas-liquid chromatography and/or mass spectroscopy, and are shown below. Cold n-hexane added to the cold trap after a collection period serves to reduce volatility so that consistent gas-liquid chromatographic samples may be obtained. In the table below, the catalyst is described as follows: percentage by weight of the rhenium compound on the alumina support, in terms of rhenium metal itself, and percentage by weight of the alkali metal hydroxide or stannate on the alumina support. The expression "conv. %" in the table refers to the percentage by weight of the isobutylene converted in one pass through the catalyst. With regard to the selectivity percentage, $C_1$ refers to methane and $C_2$–$C_3$ refer to saturated and unsaturated hydrocarbons containing the number of carbon atoms indicated in the subscripts.

CONVERSION OF ISOBUTYLENE OVER RHENIUM CATALYSTS

| Example No. | Catalyst (On Alumina) | Temp. °C. | Conv. % | Selectivity, % $C_1$ | $C_2$ | $C_3$ |
|---|---|---|---|---|---|---|
| V | 4.6% Re | 550 | 9.7 | 10.5 | 1.7 | 6.3 |
| VI | 4.6% Re/ 8.7% Na$_2$SnO$_3$ | 550 600 | 7.5 14.1 | 13.8 28.7 | 1.2 2.2 | 6.6 16.6 |
| VII | 4.6% Re/5% NaOH | 550 600 | 8.2 13.7 | 14.4 28.0 | 1.0 1.6 | 7.2 9.8 |

| Example No. | Selectivity % i-butane | benzene | toluene | p-xylene | m-xylene | o-xylene |
|---|---|---|---|---|---|---|
| V | 54.8 | 2.5 | 1.3 | 18.6 | 4.2 | trace |
| VI | 45.5 | trace | 1.8 | 31.1 | 0 | 0 |
|  | 30.5 | 4.0 | 3.2 | 40.4 | 2.7 | 1.8 |
| VII | 40.2 | 2.9 | 1.9 | 32.5 | 0 | 0 |
|  | 28.3 | 2.0 | 2.9 | 26.1 | 1.3 | 0 |

What is claimed is:

1. A catalytic composition which is prepared by a process which consists essentially of impregnating a neutral or weakly acidic support with an aqueous solution of a non-halogen containing water soluble rhenium compound before or after impregnating the support with an alkali metal hydroxide or stannate, with the proviso that the support is calcined after impregnation with said rhenium compound, and then reducing the impregnated support with hydrogen at elevated temperatures sufficient to reduce the rhenium component to its metallic state while leaving the alkali metal hydroxide or stannate largely unreduced.

2. The catalytic composition of claim 1 wherein said catalyst is on a silica or alumina support.

3. The catalytic composition of claim 2 wherein said alkali metal hydroxide or stannate is sodium hydroxide, sodium stannate, potassium hydroxide or potassium stannate.

4. The catalytic composition of claim 3 wherein said water soluble rhenium compound is ammonium perrhenate or rhenium heptaoxide.

5. The catalytic composition of claim 4 wherein said alkali metal hydroxide is sodium hydroxide or sodium stannate.

6. The catalytic composition of claim 11 wherein the support is impregnated with said rhenium compound, calcined and then impregnated with said alkali metal hydroxide or stannate.

* * * * *